(12) United States Patent
Seddon et al.

(10) Patent No.: US 8,345,407 B2
(45) Date of Patent: Jan. 1, 2013

(54) LOW VISCOSITY IONIC LIQUIDS

(75) Inventors: Kenneth Richard Seddon, Donaghadee (IE); Tayeb Belhocine, Belfast (IE); Alberto V. Puga, Belfast (IE); Keith Whiston, Darlington (GB)

(73) Assignee: Invista North America S.A R.L., Wilmington, DE (US)

( * ) Notice: Subject to any disclaimer, the term of this patent is extended or adjusted under 35 U.S.C. 154(b) by 8 days.

(21) Appl. No.: 13/023,070

(22) Filed: Feb. 8, 2011

(65) Prior Publication Data

US 2012/0050945 A1    Mar. 1, 2012

(30) Foreign Application Priority Data

Feb. 12, 2010  (GB) .................................. 1002456.0

(51) Int. Cl.
  *H01G 9/02*  (2006.01)
(52) U.S. Cl. ........ 361/504; 361/502; 361/503; 361/509; 361/512; 361/525
(58) Field of Classification Search .................. 361/502, 361/503–504, 509–512, 516–519, 523–525, 361/528–530, 535–540; 252/62.2
See application file for complete search history.

(56) References Cited

U.S. PATENT DOCUMENTS

| | | | |
|---|---|---|---|
| 6,535,373 B1 * | 3/2003 | Smith et al. .................... | 361/504 |
| 7,157,588 B2 | 1/2007 | Harmer et al. | |
| 7,167,353 B2 * | 1/2007 | Yuyama et al. ............... | 361/502 |
| 7,776,810 B2 * | 8/2010 | Jordan et al. .................. | 510/329 |
| 7,928,053 B2 * | 4/2011 | Hecht et al. ................... | 510/407 |
| 7,951,495 B2 * | 5/2011 | Otsuki et al. .................. | 429/339 |
| 8,114,318 B2 * | 2/2012 | Kuang et al. .................. | 252/580 |
| 8,116,069 B2 * | 2/2012 | Tani et al. ..................... | 361/525 |

FOREIGN PATENT DOCUMENTS

| | | |
|---|---|---|
| WO | WO2006/136529 A1 | 12/2006 |
| WO | WO2008/150842 A1 | 12/2008 |

OTHER PUBLICATIONS

Lazzari et al., Journal of the Electrical Society, 156 (8) A661-A666 (2009).
S. Alunni et al., Journal of Organic Chemistry, 1995, 60, 8371-8374.
Electrochemical Aspects of Ionic Liquids: Chapter 4: Electrochemical Windows of Room Temperature Ionic Liquids; Matsumoto, ISBN 0-471-64851-5.

* cited by examiner

*Primary Examiner* — Nguyen T Ha

(57) ABSTRACT

Disclosed is an ionic liquid:

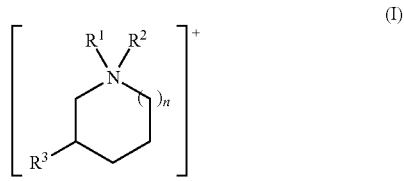

wherein:
n is 1 or 2;
$R^1$ is selected from H and $(C_1$-$C_6)$alkyl;
$R^2$ is selected from $—(CH_2)_wO[(CH_2)_xO(CH_2)_y]_m(CH_2)_z CH_3$ and

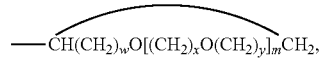

wherein w is 1 to 6, x is 1 to 6, y is 0 to 6, z is 0 to 6, m is 0 to 3 and
$[w+m(x+y)+z]$ is less than or equal to 12; and
$R^3$ is selected from H and methyl, wherein
if n is 1 then $R^3$ is methyl, and
if n is 2 then $R^3$ is H.
Also disclosed are electrochemical devices and devices employing such electrochemical devices as energy sources.

21 Claims, 2 Drawing Sheets

LOW VISCOSITY IONIC LIQUIDS

RELATED APPLICATION

This application claims benefit to GB2400 Application No. 1002456.0 filed Feb. 12, 2010 in the United Kingdom which is herein incorporated by reference in its entirety.

FIELD OF THE INVENTION

This invention relates to a class of heterocyclic compounds that are useful as ionic liquids and to uses of these ionic liquids. More particularly the invention relates to ionic liquids having certain favorable physical properties such as particularly low viscosities, low melting points and wide electrochemical windows which results in the liquids being suitable for use in a range of applications.

BACKGROUND OF THE INVENTION

An ionic liquid is a liquid that contains essentially only ions, i.e., molten salts, although some ionic liquids are in a dynamic equilibrium wherein the majority of the liquid is made up of ionic species rather than molecular species. As used herein, the term "ionic liquids" refers to liquids composed of ions. In one embodiment, the term "ionic liquids" refers to liquids composed of ions which are liquid at or below about 100° C.

Ionic liquids generally consist of salts of organic cations. The organic cations are generally bulky and asymmetric such as N-methyl-N-alkylpyrrolidinium, N-alkylpyridinium, 1-alkyl-3-alkylimidazolium, and tetraalkylammonium ions. A number of different anions may be employed, from halides to inorganic anions such as hexafluorophosphate and tetrafluoroborate and to large organic anions like bis(trifluoromethanesulfonyl)imide, trifluoroacetate or toluene-4-sulfonate. For instance, U.S. Pat. No. 7,157,588 B2 teaches compositions based on N-substituted pyrrolidinones having a pendant ammonium cation separated from the pyrrolidone ring by a variable length alkyl spacer. WO 2006/136529 teaches pyrazolium alkylsulfates and a method for their production.

More recent developments in ionic liquids have been described in WO 2008/150842 which discusses a broad class of ionic liquids comprising heterocyclic nitrogen containing cations. However, the physical properties of this broad class of ionic liquids are not investigated in any detail and thus the suitability of the liquids in specific applications is not appreciated.

Lazzari et al. (Journal of The Electrochemical Society, 156 (8) A661-A666, 2009) discusses the use of a single ionic liquid N-methoxyethyl-N-methylpyrrolidinium bis(trifluoromethanesulfonyl)imide as an electrolyte in asymmetric electrochemical double-layer carbon supercapacitors (AEDLCs). The disclosure of Lazzari et al. relates specifically to the study of the power and energy performance of AEDLCs based on N-methoxyethyl-N-methylpyrrolidinium bis(trifluoromethanesulfonyl)imide and there is no discussion of other types of ionic liquid or their physical properties or uses.

The inventors have identified a particular class of ionic liquids having certain favorable properties which makes them suitable for use in a range of applications. The ionic liquids of the invention have one or more of the following advantageous properties when compared to the ionic liquids known in the art; low viscosity, wide electrochemical window and low melting point. Therefore, the invention is able to provide the use of these ionic liquids in a range of applications in which these favorable properties can be exploited.

SUMMARY OF THE INVENTION

It is one object of the current invention to provide an ionic liquid comprising a cation according to formula (I);

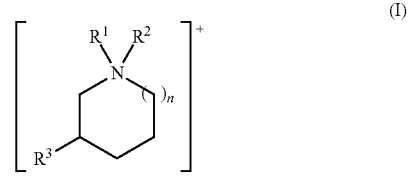

wherein:
n is 1 or 2;
$R^1$ is selected from H and $(C_1-C_6)$alkyl;
$R^2$ is selected from $-(CH_2)_wO[(CH_2)_xO(CH_2)_y]_m(CH_2)_z$ $CH_3$ and

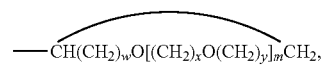

wherein w is 1 to 6, x is 1 to 6, y is 0 to 6, z is 0 to 6, m is 0 to 3 and
$[w+m(x+y)+z]$ is less than or equal to 12; and
$R^3$ is selected from H and methyl, wherein
if n is 1 then $R^3$ is methyl, and
if n is 2 then $R^3$ is H.

It is another object of the current invention to provide a method for the preparation of an ionic liquid according to formula (I) wherein the method comprises at least one N-substitution of the compound of formula (II) below:

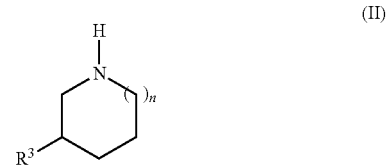

wherein;
n is 1 or 2,
$R^3$ is selected from H and methyl, wherein;
if n is 1 then $R^3$ is methyl, and
if n is 2 then $R^3$ is H.

It is another object of the current invention to provide an electrochemical device comprising an ionic liquid as hereinbefore described.

DETAILED DESCRIPTION

Figure 1A:
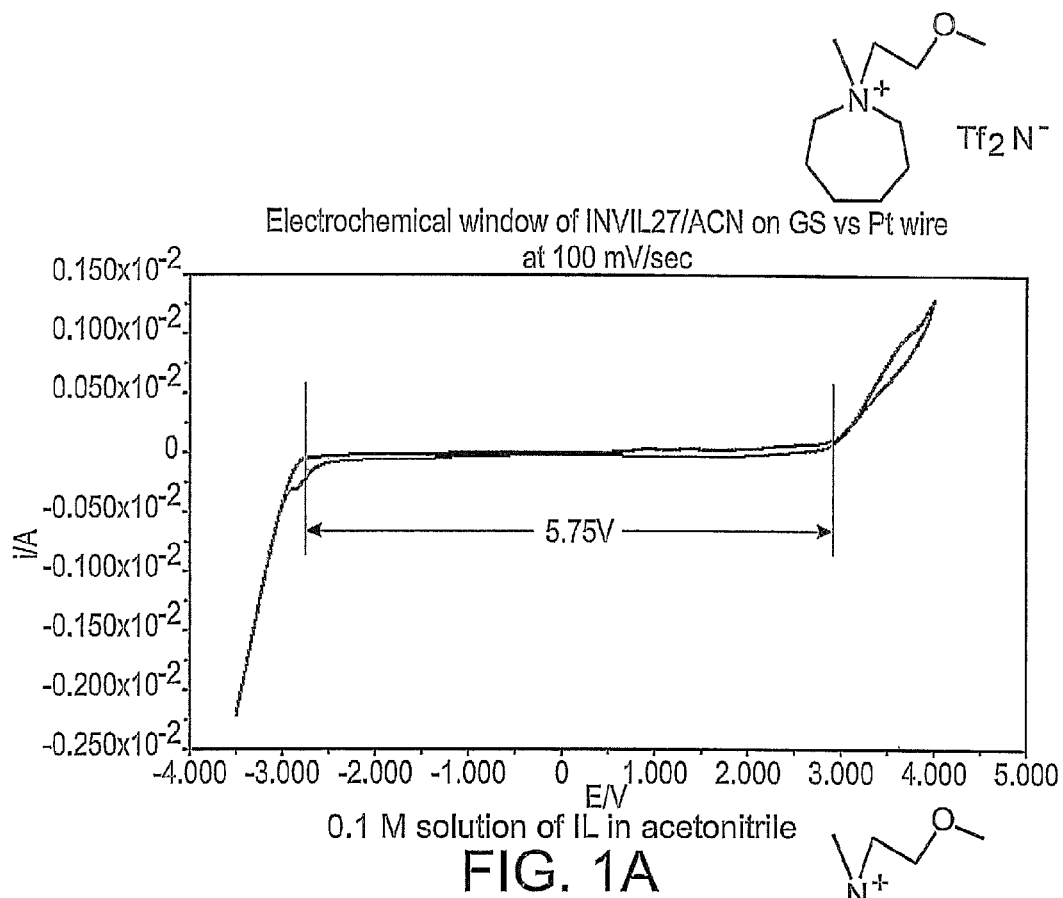
FIG. 1A is a chart depicting the electrochemical window for a preferred ionic liquid in an acetonitrile solution.

According to the invention there is provided an ionic liquid comprising a cation according to formula (I);

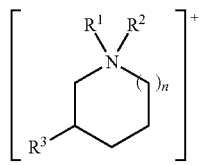

(I)

wherein:
n is 1 or 2;
$R^1$ is selected from H and $(C_1-C_6)$alkyl;
$R^2$ is selected from $—(CH_2)_wO[(CH_2)_xO(CH_2)_y]_m(CH_2)_zCH_3$ and

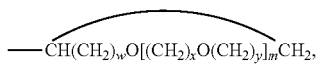

wherein w is 1 to 6, x is 1 to 6, y is 0 to 6, z is 0 to 6, m is 0 to 3 and
[w+m(x+y)+z] is less than or equal to 12; and
$R^3$ is selected from H and methyl, wherein
if n is 1 then $R^3$ is methyl, and
if n is 2 then $R^3$ is H.

There is also provided an ionic liquid comprising a subset of the cations of formula (I), wherein:
n is 1 or 2;
$R^1$ is methyl;
$R^2$ is $—(CH_2)_wO[(CH_2)_xO(CH_2)_y]_m(CH_2)_zCH_3$, where w is 1 or 2, x is 1 or 2, y is 0 to 2, z is 0 to 2 and m is 0 or 1;
$R^3$ is selected from H and methyl, wherein;
if n is 1 then $R^3$ is methyl; and
if n is 2 then $R^3$ is H.

In a further subset there is provided an ionic liquid comprising a cation of formula (I), wherein:
n is 2;
$R^1$ is methyl;
$R^2$ is $—(CH_2)_wO[(CH_2)_xO(CH_2)_y]_m(CH_2)_zCH_3$, where w is 1 or 2, x is 1 or 2, y is 0 to 2, z is 0 to 2 and m is 0 or 1; and
$R^3$ is H.

The invention also comprises the following aspects and combinations thereof.

In one aspect, the invention provides an ionic liquid comprising a cation according to formula (I), wherein $R^2$ is $—(CH_2)_wO[(CH_2)_xO(CH_2)_y]_m(CH_2)_zCH_3$, where w is 1 or 2, x is 1 or 2, y is 0 to 2, z is 0 to 2 and m is 0 or 1.

In another aspect, the invention provides an ionic liquid comprising a cation according to formula (I), wherein $R^2$ is selected from $—(CH_2)_2OCH_3$ or $—(CH_2)_2O(CH_2)_2OCH_3$.

In one aspect, the invention provides an ionic liquid comprising a cation according to formula (I), wherein $R^1$ is methyl.

In one aspect, the invention provides an ionic liquid comprising a cation according to formula (I), wherein n is 1 and $R^3$ is methyl.

In another aspect, the invention provides an ionic liquid comprising a cation according to formula (I), wherein n is 2 and $R^3$ is H.

In one aspect, the invention provides an ionic liquid comprising a cation according to formula (I), wherein the cation is selected from, 1-(2-methoxyethyl)-1-methylazepanium; 1-[2-(2-methoxyethoxy)ethyl]-1-methylazepanium; 1-(2-methoxyethyl)-1,3-dimethylpiperidinium; and 1-[2-(2-methoxyethoxy)ethyl]-1,3-dimethylpiperidinium.

The ionic liquids of the invention have favorable viscosity and this enables their use in a range of applications, particularly as low temperature lubricants or as electrolytes in electrochemical devices.

Thus, in one aspect, the invention provides an ionic liquid comprising a cation according to formula (I) wherein the viscosity of the liquid is less than 300 cP at 25° C. Preferably the viscosity of the liquid is less than 150 cP at 25° C.

The ionic liquids of the invention also have a surprisingly large "liquidous" range, i.e., the temperature range within which the materials are in the liquid state is wide, which is particularly a result of the low melting points of the liquids. This is particularly advantageous because it allows the liquids to be used in conditions of relatively high and low temperature whilst still retaining their particular properties (for example their conductivity). In one aspect, the ionic liquids of the invention have a melting point of 0° C. or below. Typically the ionic liquids have a melting point of −50° C. or below and in one embodiment the ionic liquids have a melting point of −70° C. or below.

In one aspect, the invention provides an ionic liquid comprising a cation according to formula (I) and further comprising an anion $X^−$, preferably selected from bis(trifluoromethylsulphonyl)imide; dicyanamide; hexahalophosphates; tetrahaloborates; halides; nitrates; sulfates; phosphates; carbonates; sulfonates (including substituted sulfonates such as trifluoromethylsulfonate); carboxylates (including substituted carboxylates such as trifluoroacetate) and silicates. In another aspect, the sulfonates and carboxylates are alkylsulfonates (such as methylsulfonate) and alkylcarboxylates (such as acetate) respectively. In one embodiment, $X^−$ is selected from bis(trifluoromethylsulphonyl)imide, dicyanamide, trifluoromethylsulphonate, and trifluoroacetate. In one embodiment, $X^−$ is bis(trifluoromethylsulphonyl)imide.

In one aspect, the invention provides an ionic liquid comprising the cation of formula (I) and the anion $X^−$, selected from 1-(2-methoxyethyl)-1-methyl-azepanium bis(trifluoromethylsulphonyl)imide; 1-[2-(2-methoxyethoxy)ethyl]-1-methyl-azepanium bis(trifluoromethylsulphonyl)imide; 1-(2-methoxyethyl)-1,3-dimethylpiperidinium bis(trifluoromethylsulphonyl)imide; and 1-[2-(2-methoxyethoxy)ethyl]-1,3-dimethylpiperidinium bis(trifluoromethylsulphonyl)imide.

The ionic liquids of the present invention have utility in electrochemical devices owing to their particularly favorable properties. For example, the ionic liquids of the present invention have a surprisingly wide electrochemical window. In one aspect, the invention provides ionic liquids having an electrochemical window greater than or equal to 5V, preferably greater than or equal to 5.5V and more preferably greater than or equal to 6V.

In one aspect, the invention provides an electrochemical device comprising an ionic liquid as hereinbefore described.

As used herein, "electrochemical device" means any device in which the ionic liquids of the invention are used as an electrolyte or a solvent. Examples of the electrochemical devices of the invention include electrochemical energy conversion systems such as batteries, electrochemical double-layer capacitors (EDLC) and asymmetric electrochemical double-layer capacitors (AEDLC).

The electrochemical devices of the invention can be used, for example, in hybrid electric vehicles (HEV). Thus, in one aspect, the invention provides a HEV containing an electrochemical device, (particularly an AEDLC) comprising an ionic liquid as hereinbefore described.

In one aspect, the invention provides the use of the ionic liquids hereinbefore described as electrolytes in an electrochemical device. For example, the invention provides the use of the ionic liquids hereinbefore described as an electrolyte in an electrochemical device (particularly an AEDLC) for example in a HEV.

In one aspect, the invention provides a method for the preparation of an ionic liquid according to formula (I) wherein the method comprises at least one N-substitution of the compound of formula (II) below:

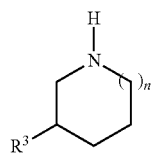

(II)

wherein;
n is 1 or 2,
$R^3$ is selected from H and methyl, wherein;
if n is 1 then $R^3$ is methyl, and
if n is 2 then $R^3$ is H.

In another aspect, the invention provides a method for the preparation of an ionic liquid according to formula (I) wherein the method comprises at least one N-substitution of the compound of formula (II) shown above, wherein: n is 2 and $R^3$ is H.

As used herein, the step of N-substitution is an N-alkylation step and comprises contacting an N-substitution agent (i.e., an N-alkylating agent) with the compound of formula (II). Such synthetic procedures are well known in the art and may be carried out using any method known to the skilled person. In an aspect of the invention, the N-substitution step is an N-alkylation. A non-limiting example of the N-alkylation of azepane is described in the Journal of Organic Chemistry, Vol. 60, No. 26, 1995, 8371-8374. It will be appreciated that the term "N-alkylation" as used herein refers to the substitution on nitrogen by an alkyl group interrupted by one or more ether oxygen atoms, for example, the group defined for $R_2$ in formula (I) above and therefore that "N-alkylating agent" as used herein refers to a substance containing an alkyl group interrupted by one or more ether oxygen atoms, for example, the group defined for $R_2$ in formula (I).

The or each N-alkylation step(s) may be carried out with any $C_1$-$C_{12}$ alkylating reagent that is capable of quaternarising the amine nitrogen of formula (II). Optionally the or each N-alkylation step is carried out using a $C_1$-$C_{12}$ alkylating agent(s) (e.g., alkyl halides, alkyl sulfonates or alkyl sulfates). For example, the $C_1$-$C_{12}$ alkylating agent is 1-bromo-2-methoxyethane.

Optionally, the or each N-substitution reaction(s) may be carried out in an inert solvent, such as acetonitrile, acetone, methanol or dichloromethane.

In one aspect, a single N-substitution step is carried out. The ionic liquid produced using the method of this embodiment has the formula described by formula (I), wherein $R^1$ is hydrogen.

In a further aspect, two N-substitution steps are carried out. The ionic liquid produced using this method has the formula described by formula (I), wherein $R^1$ is not hydrogen.

The two N-substitution steps may be carried out sequentially or simultaneously and are conveniently carried out sequentially.

Optionally, the two N-substitution steps are carried out sequentially. Conveniently, the first N-substitution step is carried out with a $C_1$-$C_{12}$ alkylating agent (e.g., alkyl halides, alkyl sulfonates or alkyl sulfates). For example, the $C_1$-$C_{12}$ alkylating agent is 1-bromo-2-methoxyethane. Optionally the second N-substitution step is carried out with the N-alkylating agent methyl iodide.

Optionally the single or first N-substitution step is carried out at a temperature below about 100° C., optionally below about 75° C., optionally below about 50° C. optionally below about 20° C.

In the aspect where there are two N-substitution steps, optionally the two N-substitution steps are carried out sequentially. The second N-substitution step is carried out at a temperature below about 100° C., optionally below about 75° C., optionally below about 50° C., optionally below about 20° C. Advantageously, after the reagents are added the reaction mixture is warmed to a temperature from about 0° C. to about 100° C., optionally from about 0° C. to about 75° C., optionally from about 0° C. to about 50° C., optionally about room temperature.

The anion component of the single or second N-substitution step may form the ionic liquid anion, $X^-$. Advantageously the anion component of the single or second N-substitution is selected from the group consisting of halides, sulfonates and sulfates.

In an alternative aspect, the method may additionally comprise the step of anion exchange of the N-substituted salt product. Prior to the anion exchange, excess N-substitution agent may be removed, for example, by evaporation. In addition, the N-substituted salt product may be washed with a solvent prior to the anion exchange step.

The anion exchange step comprises contacting the N-substituted solution product with an ion exchange agent, optionally in an inert atmosphere. Advantageously the anion exchange step is carried out at a temperature of from about 0° C. to about 100° C., optionally from about 0° C. to about 75° C., optionally from about 0° C. to about 50° C., optionally about room temperature. Advantageously the N-substituted solution product and the ion exchange agent are contacted and stirred for several hours (e.g., from about 0.5 to about 24 hours, optionally from about 1 to about 15 hours, optionally from about 4 to about 12 hours). The ion exchange agent comprises an $X^-$ anion as defined above but which is different to the anion component of the single or second N-substitution step present in the product obtained from the single or second N-substitution step.

Optionally the ion exchange agent is a metal salt of the anion $X^-$, defined previously. Optionally, the metal is an alkali metal or an alkaline earth metal.

The optional anion exchange step is typically conducted in solution. Solvents used in the anion exchange reaction should be inert to the reactants and the products and include methanol, ethanol, acetone, acetonitrile and water, preferably water. The composition comprising the desired anion can then be recovered using a suitable technique such as evaporation or the reactant solvent, decantation, re-crystallisation and/or filtration.

In another aspect, the anion exchange agent may be contacted with the N-substituted salt product and mixed in a solvent for a period of time, i.e., more than about 5 hours. The composition comprising the desired anion can then be recovered using a suitable technique such as evaporation or the reactant solvent, decantation, re-crystallisation and/or filtration.

In one aspect, formula (II) represents azepane. The azepane represented by formula (II) may be a by-product of the manufacture of 1,6-hexanediamine. In a further aspect, formula (II) may represent 3-methylpiperidine. The 3-methylpiperidine represented by formula (II) may be a by-product of the manufacture of 2-methyl-1,5-pentanediamine. In these by-product aspects, the 1,6-hexanediamine may be produced by the hydrogenation of hexanedinitrile and the 2-methyl-1,5-pentanediamine may be produced by the hydrogenation of 2-methylpentanedinitrile.

In this aspect, the hydrogenation reactions are optionally carried out in the presence of hydrogen gas and a catalyst, e.g., an iron catalyst or a Raney cobalt catalyst. The hydrogenation reactions are optionally carried out at an elevated temperature (e.g., from about 30° C. to about 500° C., optionally from about 50° C. to about 350° C., optionally from about 80° C. to about 200° C., optionally from about 80° C. to about 150° C.). The hydrogenation reactions are optionally carried out at elevated pressure (e.g., from about 400 psig to about 8000 psig, optionally from about 1000 psig to about 6000 psig, optionally about 1500 psig to about 5000 psig, optionally from about 3000 psig to about 5000 psig). Advantageously, when using an iron catalyst, the hydrogenation reaction is carried out at a temperature of from 80° C. to about 200° C., optionally about 140° C. and/or a pressure of from about 1500 psig to about 5000 psig, optionally about 4500 psig. Advantageously, when using a Raney cobalt catalyst, the hydrogenation reaction is carried out at a temperature of from 80° C. to about 150° C., optionally about 115° C. and/or a pressure of from about 400 psig to about 2500 psig, optionally about 800 psig. Optionally the compound of formula II is separated from the product mixture, i.e., the crude 1,6-hexanediamine or 2-methyl-1,5-pentanediamine, by distillation at reduced pressure and elevated temperature.

As used herein, the term "alkyl" means a branched or unbranched, saturated or unsaturated (i.e., alkenyl or alkynyl) hydrocarbyl radical which may be substituted or unsubstituted. The alkyl group is optionally $C_1$ to $C_{10}$, optionally $C_1$ to $C_6$, optionally methyl, ethyl, propyl(n-propyl or isopropyl), butyl(n-butyl, isobutyl or tertiary-butyl) or pentyl (including n-pentyl and iso-pentyl), optionally methyl. It will be appreciated therefore that the term "alkyl" as used herein includes alkyl (branched or unbranched), alkenyl (branched or unbranched) and alkynyl (branched or unbranched). In one aspect, the term "alkyl" means a branched or unbranched saturated hydrocarbyl radical.

An alkyl group may be substituted with one or more substituents wherein possible substituents include alkyl; aryl; arylalkyl (e.g., substituted and unsubstituted benzyl, including alkylbenzyl); halogen atoms and halogen-containing groups such as haloalkyl (e.g., trifluoromethyl) or haloaryl (e.g., chlorophenyl); hydroxyl; carboxyl (e.g., carboxaldehyde, alkyl- or aryl-carbonyl, carboxy, carboxyalkyl or carboxyaryl), amide and nitrile.

As used herein, the term "aryl" means a carbocyclic aromatic group, such as phenyl or naphthyl (optionally phenyl).

The aryl group may be substituted with one or more substituents wherein possible substituents include alkyl; awl; arylalkyl (e.g., substituted and unsubstituted benzyl, including alkylbenzyl); halogen atoms and halogen-containing groups such as haloalkyl (e.g., trifluoromethyl) or haloaryl (e.g., chlorophenyl); hydroxyl; carboxyl (e.g., carboxaldehyde, alkyl- or aryl-carbonyl, carboxy, carboxyalkyl or carboxyaryl), amide and nitrile. Optionally the awl group is unsubstituted.

In one aspect, the groups of $R_2$, $-(CH_2)_wO[(CH_2)_xO(CH_2)_y]_m(CH_2)_zCH_3$ and

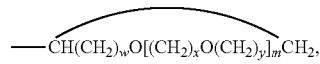

are each optionally substituted on one or more carbon atoms with one or more groups selected from alkyl or aryl.

In groups such as $-(CH_2)_wO[(CH_2)_xO(CH_2)_y]_m(CH_2)_zCH_3$ and

"—" denotes the point of attachment of the group to the remainder of the molecule.

As used herein, the term "halogen" means a fluorine, chlorine, bromine or iodine radical. Typically, "halogen" means a fluorine radical.

The ionic liquid according to formula I comprises an anion, $X^-$, optionally selected from the group consisting of: bis(trifluoromethylsulphonyl)imide; dicyanamide; hexahalophosphates (conveniently hexafluorophosphate or hexachlorophosphate); tetrahaloborates (optionally tetrafluoroborate or tetrachloroborate); halides; nitrates; sulfates; phosphates; carbonates; sulfonates; carboxylates and silicates.

The sulfates and sulfonates may be selected from the group consisting of sulfate, hydrogen sulfate, alkyl or aryl sulfate, alkyl or aryl sulfonates, methanesulfonate, trifluoromethanesulfonate, and toluene-4-sulfonate, alkyl or aryl oxoanion sulfates. Conveniently the oxoanion sulfates are selected from persulfate ($SO_5^{2-}$), sulfite ($SO_3^{2-}$), hyposulfite ($SO_2^{2-}$), peroxydisulfite ($S_2O_8^{2-}$).

The phosphates may be selected from the groups consisting of: phosphate; hydrogen phosphate; dihydrogen phosphate, alkyl or aryl phosphate, alkyl or aryl phosphonates, alkyl or aryl phosphinates, other oxoanion phosphates and metaphosphate.

The carbonates may be selected from the group consisting of carbonate and hydrogen carbonate, alkyl or aryl carbonates and other oxoanion carbonates.

The carboxylates may be selected from the group consisting of: alkylcarboxylates; arylcarboxylates and ethylenediaminetetraacetate.

As used herein, the term "alkylcarboxylates" refers to alkyl compounds with one or more carboxylate groups, conveniently one, two or three carboxylate groups. Alkylcarboxylates include formate; acetate, propanoate, butanoate, pentanoate, hexanoate, heptanoate, octanoate, nonanoate, decanoate, oxalate; succinate; crotonate; fumarate. The term "alkylcarboxylates", as used herein, further includes carboxylates wherein the alkyl group is substituted with the substituent groups referred to herein and therefore further includes glycolate; lactate; tartrate; hydrogen tartrate; malate; citrate; trifluoroacetate; pentafluoropropanoate; heptafluorobutanoate; mandelate; and phenylacetate.

As used herein, the term "arylcarboxylates" refers to aryl compounds with one or more pendant carboxylate groups, conveniently one, two or three carboxylate groups. Arylcarboxylates include benzoate; benezenedicarboxylate; benzenetricarboxylate; benzenetetracarboxylate; chlorobenzoate; fluorobenzoate; pentachlorobenzoate; pentafluorobenzoate and salicylate.

Conveniently X$^-$ is dicyanamide or bis(trifluoromethanesulfonyl)imide.

Electrochemical Window

The electrochemical window of a substance is a measure of its stability over a range of applied voltages. The electrochemical window can be expressed as the potential (i.e., voltage) range over which the substance is neither oxidised nor reduced, or as a discrete value calculated as the potential difference between the reduction potential and the oxidation potential.

Electrochemical window can be measured using cyclic voltametry and linear sweep voltametry according to techniques established in the art (*Electrochemical Aspects of Ionic Liquids; Chapter 4: Electrochemical Windows of Room Temperature Ionic Liquids*; Matsumoto, ISBN 0-471-64851-5).

In the present invention, the electrochemical window of the ionic liquids was calculated using the cyclic voltametry method described below.

Voltammetric experiments were carried out in a 10 cm$^3$ glass cell with 3 g of ionic liquid. Cyclic voltammogram experiments were recorded with a PC-controlled microAutolab Type III Potentiostat, and performed in a three-electrode arrangement with a glassy carbon (3 mm diameter), a bright platinum coil as the counter electrode, and all potentials measured with respect to a 0.01 M Ag$^+$/Ag reference, with AgNO$_3$ dissolved in [C$_4$mim][NO$_3$] and separated from the bulk solution via a glass frit. For acetonitrile solution, a similar reference was employed with AgNO$_3$ dissolved in a solution of 0.1 M [N$_{4444}$][ClO$_4$] in acetonitrile. The IR-drop was uncompensated. The glassy carbon (GC) electrode was polished using diamond pastes (Kemet, UK) of decreasing particle size (6–/0.1 μm) on soft lapping pads. Prior to all experiments, all solutions were purged by bubbling argon for at least 10 min (argon gas dried by passing through a column of 4 Å molecular sieves). A positive pressure of inert gas was maintained above the surface of the electrolyte throughout the experiments. Acetonitrile was refluxed and distilled over CaH$_2$.

For acetonitrile/IL solution, 0.1 M solution of the relevant IL was used. In the case of the pure IL, mass transfer is decreased by several factors of magnitude. This results in much less steep solvent oxidation/reduction processes, with a resulting elongation of the electrochemical window when compared with equivalent dilute solutions in a non-aqueous solvent. Therefore the derivative of the scan was used, and the electrochemical window defined as the midpoint in the sudden change in gradient observed as oxidation or reduction of the IL. These electrochemical windows are more conservative that those typically obtained using solutions in non-aqueous solvents (and arguably more relevant to real applications).

Figure 1B:
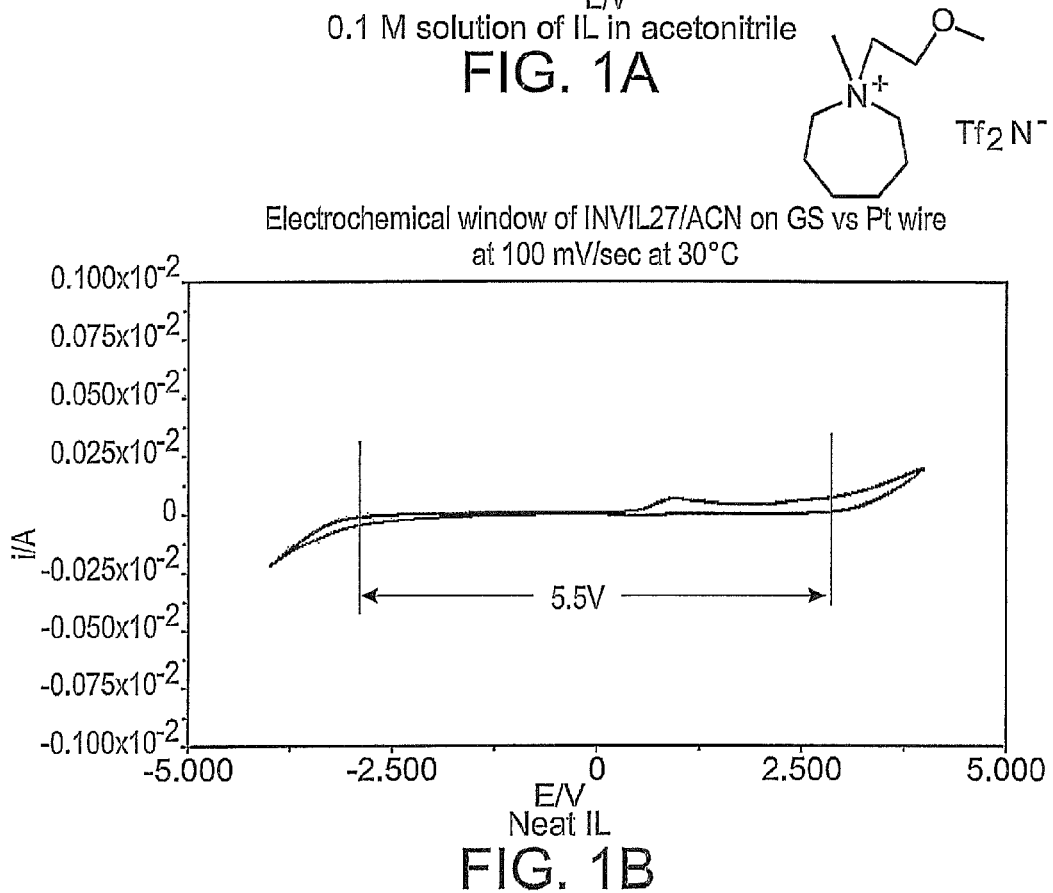
FIG. 1B is a chart depicting the electrochemical window for a neat preferred ionic liquid.

An internal standard such as ferrocene was not employed. The Ag/Ag$^+$ reference electrodes employed had a potential of around −0.1 V vs. ferrocene/ferrocenium. The electrochemical windows of the different ILs are depicted in Table 1. An example of a cyclic voltammogram (CV) for [MeO(CH$_2$)$_2$-mHMI NTf$_2$] as a 0.1 M solution in acetonitrile (a) and neat (b) are shown in FIG. 1A and FIG. 1B. Unless stated otherwise, measurements were carried out at 25° C.

Viscosity

Measurement of viscosity was made using a Brookfield DV-II+PRO digital viscometer. Before use, all the ionic liquids were dried using a heated oil bath at 60° C. while subjected to a vacuum and left overnight to facilitate maximum water removal. The temperature for viscosity measurement could be controlled using a water bath (GRANT LTD6G) and were set to 25° C. To minimize the uncertainty caused by temperature equilibrium, all measurements were performed in triplicate or until constant reading obtained by taking each reading at 10 min intervals. The repeatability of the viscosity measurements was ±0.2%.

The viscosities of the different ionic liquids are shown in Table 1.

Melting Point

Melting points were determined by differential scanning calorimetry (TA DSC Q2000 with either liquid nitrogen cryostatic cooling or a refrigerated cooling system, 5-20 mg samples, 5 C min$^{-1}$ heating and cooling rates under dinitrogen, scanning between −100 and +120° C.).

Melting points (T$_m$, onset of the endothermic peak) were recorded on heating in the second heating/cooling cycle for each salt.

Figure 2:
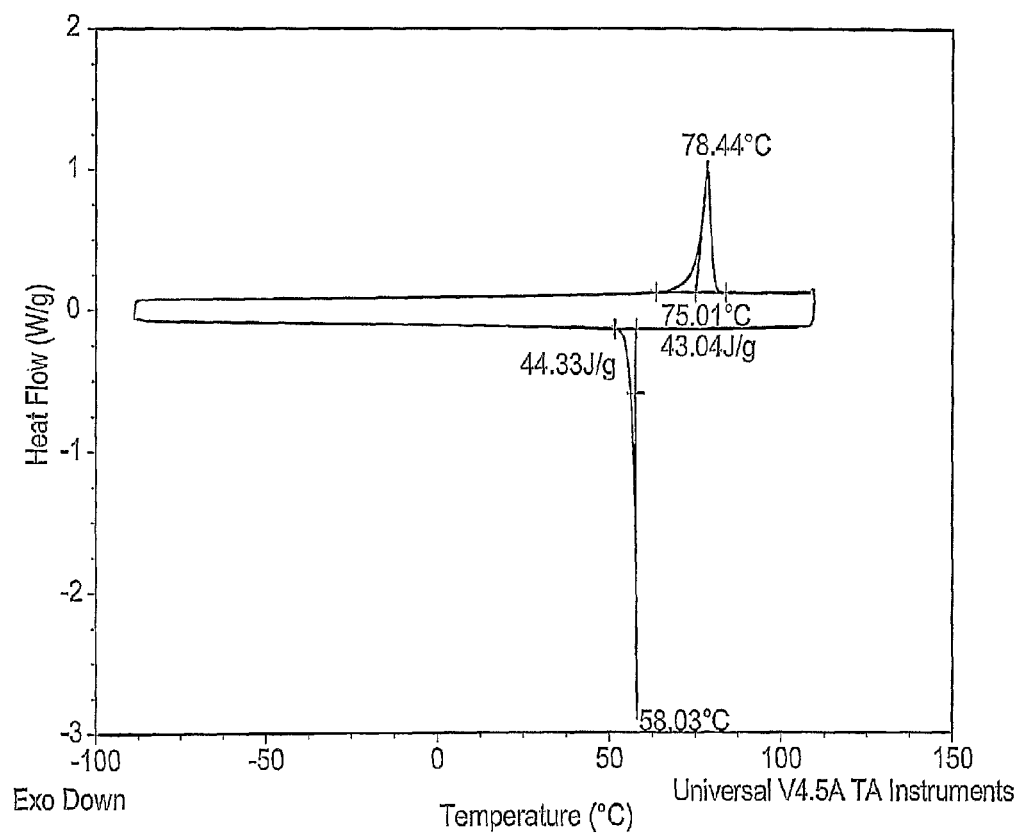
FIG. 2 is a chart depicting a differential scanning calorimetry (DSC) trace for a preferred ionic liquid.

The melting points of the different ionic liquids are shown in Table 1. An example of a DSC trace for a comparative ionic liquid is shown in FIG. 2.

The DSC method applied to pure materials, i.e., those having a sharp melting point, is known to the skilled practitioner. The DSC instrument is calibrated using a pure sample of indium metal. In the determination of a melting point for a pure material the characteristic temperatures associated with an endotherm are recorded. These temperatures are the onset of the endotherm and the peak temperature. In the case of pure materials, the choice of which temperature to take as the melting point is not critical as the endotherm is very sharp.

Electrochemical Double-Layer Capacitor (EDLC)

Electrochemical double-layer capacitors, also known as supercapacitors or ultracapacitors, are electrochemical capacitors that have an unusually high energy density when compared to common capacitors, typically in the order of thousands of times greater than a high capacity electrolytic capacitor. They typically contain two electrodes (a positive electrode and a negative electrode).

Electric double-layer capacitors have a variety of commercial applications, some of the earliest uses were motor startup capacitors for large engines. More recently they have become a topic of some interest in the green energy world, where their ability to store energy quickly makes them particularly suitable for regenerative braking applications, whereas batteries have difficulty in this application due to slow charging rates. New technology in development could potentially make EDLCs with high enough energy density to be an attractive replacement for batteries in all-electric cars and plug-in hybrids, as EDLCs are quick charging and exhibit temperature stability.

The performance of EDLCs depends, amongst other things, on the substance used as the electrolyte within the device. The ionic liquids of the invention are particularly suited to this application owing to their favorable properties.

Asymmetric Electrochemical Double-Layer Capacitor (AEDLC)

Conventional EDLCs, sometimes referred to as "symmetric" electrochemical double-layer capacitors, employ materials having approximately the same level of response to an applied voltage for both electrodes whereas asymmetric electrochemical double-layer capacitors utilize two different materials for the electrodes, each having a differing magnitude of response to an applied voltage. Alternatively "symmetric" electrochemical double-layer capacitors can be described as those employing the same mechanism of energy storage at both electrodes and asymmetric electrochemical double-layer capacitors can be described as those employing different mechanisms of energy storage at each electrode.

Mechanisms of energy storage include charge separation and faradaic processes (electron transfer).

As with EDLCs, the performance of AEDLCs depends, amongst other things, on the substance used as the electrolyte within the device. The ionic liquids of the invention are particularly suited to this application owing to their favorable properties.

Hybrid Electric Vehicles (HEV)

There is a continuing need to provide more environmentally friendly energy production methods, particularly within the automotive industry. In recent years attention has turned to the production of hybrid electric vehicles, that is, vehicles which combine a conventional internal combustion engine propulsion system with an electric propulsion system. The market success of clean transportation by HEVs needs high efficiency, safe and low cost electrochemical energy conversion systems. The performance requirements of these systems depend on the level of power-train hybridization, which increases from mild to full and plug-in HEVs, and on the kind of driving cycle. For power-assist HEVs (i.e., full HEVs with the highest level of hybridisation), lithium ion batteries are considered to be the best candidates. EDLCs currently on the market do not satisfy the minimum energy requirements for use in full HEVs, and so, despite their high safety and tolerability, they are not preferred candidates for use in full HEVs. If the energy output of EDLCs could be improved, these devices could compete with lithium ion batteries in power-assist HEVs, with the advantage of higher safety and tolerability.

The invention is further illustrated by the following examples. It will be appreciated that the examples are for illustrative purposes only and are not intended to limit the invention as described above. Modification of detail may be made without departing from the scope of the invention.

EXAMPLES

Electrospray mass spectroscopy was performed by The Analytical Services and Environmental Projects Unit, Queens University Belfast.

$^1$H and $^{13}$C NMR spectra were recorded on Bruker Avance DRX 500 and DPX 300 spectrometers in $CDCl_3$.

Melting points and glass transition temperatures were determined by differential scanning calorimetry as discussed above.

Comparative Example 1a 1-butyl-1-methylazepanium bis(trifluoromethylsulfonyl)imide Procedure 1a—The first N-substitution of azepane was carried out using butyl bromide as an N-alkylating agent to form 1-butylazepane. To a stirring solution of azepane (49.97 g, 503.8 mmol) in methanol (220 cm$^3$) cooled in an ice-water bath was added dropwise 1-bromobutane (57 cm$^3$, 530 mmol), and then potassium carbonate (72.5 g, 524 mmol). The mixture was vigorously stirred at room temperature for 24 h. The resulting suspension was filtered through a sintered glass fret and the solution concentrated under reduced pressure at 45° C. in a rotary evaporator. A yellowish suspension was thus obtained and distilled in vacuo (45-47° C., 5.5 mmHg) to give 1-butylazepane as a colourless liquid (50.30 g, 64.3%). $\delta_H$ (500.13 MHz, $CDCl_3$) 2.62 (4H, t, $^3$J(H,H)=5.5 Hz), 2.45 (2H, m), 1.64 (4H, br m), 1.59 (4H, br m), 1.45 (2H, m), 1.30 (2H, sextet, $^3$J(H,H)=7.4 Hz), 0.90 (3H, t, $^3$J(H,H)= 7.4 Hz); $\delta_C$ (125.76 MHz, $CDCl_3$) 58.2, 55.7, 29.8, 28.0, 27.1, 20.9, 14.1. ESI-MS: m/z=156 [M+H]$^+$ (100). Calcd. for $C_{10}H_{22}N$: 156.1752; found: 156.1755.

Procedure 1b—Following this, a second N-substitution was carried out on the 1-butylazepane using methyl iodide as an N-alkylating agent to form 1-butyl-1-methylazepanium iodide. A slight excess of methyl iodide was added dropwise to 1-butylazepane in dichloromethane keeping the temperature below 20° C. by an ice-water bath. The reaction mixture was then allowed to warm to room temperature and stirred until complete conversion of amine (as determined using $^1$H NMR). Diethyl ether was then added to the reaction mixture and the white precipitate (1-butyl-1-methyl-azepanium iodide) filtered, washed with ether and dried in air. $\delta_H$ (300 MHz, $CDCl_3$) 3.40 (4H, m), 3.30 (2H, m), 3.02 (3H, s), 1.90 (4H, m), 1.78 (6H, m), 1.40 (2H, m), 1.00 (3H, t).

Procedure 1c—A slight excess of lithium bis(trifluoromethylsulfonyl)imide dissolved in water was added to an aqueous solution of 1-butyl-1-methyl-azepanium iodide and stirred at room temperature for approximately 5 hours. The reaction mixture was transferred to a separating funnel and the heavy layer washed several times with water. The addition of a small amount of dichloromethane aided the separation of the aqueous and organic layer. The heavy organic layer was then evaporated to dryness leaving a pale yellow liquid, 1-butyl-1-methylazepanium bis(trifluoromethylsulfonyl)imide. $\delta_H$ (500.13 MHz, $CDCl_3$) 3.42 (2H, m), 3.36 (2H, m), 3.22 (2H, m), 3.02 (3H, s), 1.88 (4H, m), 1.73 (6H, m), 1.40 (2H, sextet), 1.00 (3H, t). $\delta_C$ (125.76 MHz, $CDCl_3$) 120 (q, $CF_3$), 65.56, 64.84, 50.55, 27.46, 24.49, 21.80, 19.54, 13.37. ESI-MS: m/z=170 [M]$^+$ (100). Calcd. for $C_{11}H_{24}N$: 170.1909; found: 170.1912, m/z=280 [M]$^-$ (100). Calcd. for $C_2F_6NO_4S_2$: 279.9173; found: 279.9163; $T_g$=−80° C.

Comparative Example 2

1-(2-methoxyethyl)-1-methylpyrrolidinium bistriflimide

A mixture of N-methylpyrrolidine (9.11 g, 0.1 mol), 1-bromo-2-methoxyethane (15.0 g, 0.107 mol) and anhydrous acetone (40 cm$^3$) was refluxed for 24 h. After evaporation under reduced pressure, the yellow solid was washed with diethylether. 1-(2-methoxyethyl)-1-methylpyrrolidinium bromide was obtained as white solid in ca. 70% yield. $\delta_H$ (500.13 MHz, $CDCl_3$) 3.95 (2H, m), 3.85 (6H, m), 3.40 (3H, s), 3.23 (3H, s), 2.29 (4H, m).

Following the procedure 1c, 1-(2-methoxyethyl)-1-methylpyrrolidinium bistriflimide was obtained as a pale yellow liquid in almost quantitative yield. $\delta_H$ (500.13 MHz, $CDCl_3$) 3.78 (2H, m), 3.59 (6H, m), 3.38 (3H, s), 3.10 (3H, s), 2.24 (4H, m). $\delta_C$ (125.76 MHz, $CDCl_3$) 122.37 (q, $CF_3$), 66.75, 66.06, 63.85, 59.46, 49.32, 21.79. ESI-MS: m/z=144 [M]$^+$ (100). Calcd. for $C_8H_{18}NO$: 144.1388; found: 144.1380, m/z=280 [M]$^-$ (100). Calcd. for $C_2F_6NO_4S_2$: 279.9173; found: 279.9182; $T_g$=−72° C.

Comparative Example 3

1-[2-(2-methoxyethoxy)ethyl]-1-methylpyrrolidinium bistriflimide

N-methylpyrrolidine (9.11 g, 0.1 mol), 1-bromo-2-(2-methoxy-ethoxy)ethane (10.0 g, 0.103 mol) and anhydrous acetone (40 cm$^3$) was refluxed for 24 h. After evaporation under reduced pressure, the yellow solid was washed with diethylether. 1-[2-(2-methoxyethoxy)ethyl]-1-methylpyrrolidinium bromide was obtained as white solid in ca. 68% yield. $\delta_H$ (500.13 MHz, CDCl$_3$) 3.98 (2H, m), 3.87 (6H, m), 3.68 (2H, m), 3.53 (2H, m), 3.40 (3H, s), 3.33 (3H, s), 2.29 (4H, m).

Following the procedure 1c, 1-[2-(2-methoxyethoxy)ethyl]-1-methylpyrrolidinium bistriflimide was obtained as a pale yellow liquid in almost quantitative yield. $\delta_H$ (500.13 MHz, CDCl$_3$) 3.90 (2H, m), 3.65 (6H, m), 3.56 (2H, m), 3.53 (2H, m), 3.35 (3H, s), 3.10 (3H, s), 2.24 (4H, m). $\delta_C$ (125.76 MHz, CDCl$_3$) 122.33 (q, CF$_3$), 71.86, 70.79, 65.99, 65.39, 63.80, 59.19, 49.20, 21.71. ESI-MS: m/z=188 [M]$^+$ (100). Calcd. for C$_{10}$H$_{22}$NO$_2$: 188.1651; found: 188.1645, m/z=280 [M]$^-$ (100). Calcd. for C$_2$F$_6$NO$_4$S$_2$: 279.9173; found: 279.9182; $T_g$=−91° C.

Example 1a

1-(2-methoxyethyl)-1-methyl-azepanium bistriflimide

1-Methoxyethylazepane was obtained using procedure 1a, from azepane (10.7 g, 0.107 mol) in methanol (50 cm$^3$), 1-bromo-2-methoxyethane (15.0 g, 0.107 mol) and potassium carbonate (15.0 g). After distillation in vacuo (42-44° C., 1.0 mmHg), 1-methoxyethylazepane was obtained as a colourless liquid in ca. 72% yield. $\delta_H$ (500.13 MHz, CDCl$_3$) 3.6 (6H, m), 3.38 (3H, s), 2.68 (2H, t), 1.59 (8H, br m). ESI-MS: m/z=158 [M+H]$^+$ (100). Calcd. for C$_9$H$_{19}$NO: 158.1545; found: 158.1535.

Following the procedure 1b, 1-(2-methoxyethyl)-1-methyl-azepanium iodide was obtained as a white solid in almost quantitative yield. $\delta_H$ (500.13 MHz, CDCl$_3$) 3.8 (2H, br m), 3.62 (2H, m), 3.49 (2H, m), 3.39 (2H, m), 3.36 (3H, s), 3.09 (3H, s), 1.88 (4H, m), 1.72 (4H, m). ESI-MS: m/z=172 [M]$^+$ (100). Calcd. for C$_{10}$H$_{22}$NO: 172.1701; found: 172.1699, m/z=126.9 [M]$^-$ (100). Calcd. For I: 126.9045; found: 126.9039.

Following the procedure 1c, 1-(2-methoxyethyl)-1-methyl-azepanium bistriflimide was obtained as a pale yellow liquid. $\delta_H$ (500.13 MHz, CDCl$_3$) 3.90 (2H, m), 3.63 (2H, m), 3.52 (2H, m), 3.41 (2H, m), 3.32 (3H, s), 3.12 (3H, s), 1.89 (4H, br m), 1.71 (4H, m). $\delta_C$ (125.76 MHz, CDCl$_3$) 122.37 (q, CF$_3$), 66.09, 65.08, 64.62, 58.99, 51.81, 27.62, 21.74. ESI-MS: m/z=172 [M]$^+$ (100). Calcd. for C$_{10}$H$_{22}$NO: 172.1701; found: 172.1686, m/z=280 [M]$^-$ (100). Calcd. for C$_2$F$_6$NO$_4$S$_2$: 279.9173; found: 279.9180; $T_g$=−75° C.

Example 2a

1-[2-(2-methoxyethoxy)ethyl]-1-methyl-azepanium bistriflimide

[2-(2-methoxyethoxy)ethyl]azepane was obtained using procedure 1a, from azepane (10.3 g, 0.103 mol) in methanol (50 cm$^3$), 1-bromo-2-(2-methoxy-ethoxy)ethane (10.0 g, 0.103 mol) and potassium carbonate (16.0 g). After distillation in vacuo (66-68° C., 1.0 mmHg), [2-(2-methoxyethoxy)ethyl]azepane was obtained as a colourless liquid in ca. 65% yield. $\delta_H$ (500.13 MHz, CDCl$_3$) 3.59 (6H, m), 3.38 (3H, s), 2.73 (2H, t), 2.68 (4H, m), 1.59 (8H, br m). ESI-MS: m/z=202 [M+H]$^+$ (100). Calcd. for C$_{11}$H$_{23}$NO$_2$: 202.1807; found: 202.1802.

Following the procedure 1b, 1-[2-(2-methoxyethoxy)ethyl]-1-methyl-azepanium iodide was obtained as a white solid in almost quantitative yield. $\delta_H$ (500.13 MHz, CDCl$_3$) 4.03 (2H, br m), 3.91 (4H, m), 3.68 (4H, m), 3.52 (2H, m), 3.40 (3H, s), 3.36 (3H, s), 2.0 (4H, br m), 1.79 (4H, m). ESI-MS: m/z=216 [M]$^+$ (100). Calcd. for C$_{12}$H$_{26}$NO$_2$: 216.1964; found: 216.1947, m/z=126.9 [M]$^-$ (100). Calcd. For I: 126.9045; found: 126.9036.

Following the procedure 1c, 1-[2-(2-methoxyethoxy)ethyl]-1-methyl-azepanium bistriflimide was obtained as a pale yellow liquid in almost quantitative yield. $\delta_H$ (500.13 MHz, CDCl$_3$) 3.94 (2H, br m), 3.65 (4H, m), 3.52 (4H, m), 3.42 (2H, m), 3.36 (3H, s), 3.17 (3H, s), 1.91 (4H, m), 1.72 (4H, m). $\delta_C$ (125.76 MHz, CDCl$_3$) 122.37 (q, CF$_3$), 71.84, 70.64, 65.88, 65.20, 64.69, 59.18, 52.12, 27.96, 22.13. ESI-MS: m/z=216 [M]$^+$ (100). Calcd. for C$_{12}$H$_{26}$NO$_2$: 216.1964; found: 216.1953, m/z=280 [M]$^-$ (100). Calcd. for C$_2$F$_6$NO$_4$S$_2$: 279.9173; found: 279.9181; $T_g$=−82° C.

Comparative Example 4 and Examples 3 and 4

1-butyl-1,3-dimethylpiperidinium bis(trifluoromethylsulfonyl)imide (Comparative Example 4)

1-[2-(2-methoxyethoxy)ethyl]-1,3-dimethylpiperidinium bis(trifluoromethylsulphonyl)imide (Example 3)

1-(2-methoxyethyl)-1,3-dimethylpiperidinium bis(trifluoromethylsulphonyl)imide (Example 4)

These examples, shown in Table 1 below, were synthesised using analogous methods to those shown above (Procedures 1a, 1b and 1c) for Comparative examples 1-3 and Examples 1 and 2.

Comparative Examples 1b and 1c and Examples 1b, 1c, 2b and 2c

1-butyl-1-methylazepanium triflate (Comparative Example 1b)

1-butyl-1-methylazepanium trifluoroacetate (Comparative Example 1c)

1-(2-methoxyethyl)-1-methylazepanium triflate (Example 1b)

1-(2-methoxyethyl)-1-methylazepanium trifluoroacetate (Example 1c)

1-[2-(2-methoxyethoxy)ethyl]-1-methylazepanium triflate (Example 2b)

1-[2-(2-methoxyethoxy)ethyl]-1-methylazepanium trifluoroacetate (Example 2c)

These examples, shown in Table 1 below, were synthesised using analogous methods to those shown above (Procedures 1a, 1b and 1e) for Comparative examples 1-3 and Examples 1 and 2. In the case of the anion exchange step (Procedure 1c above) the procedure was modified to use an ion exchange agent to obtain the relevant anion, as discussed above in connection with the anion exchange step.

Experimental Data

Measurements were carried out, as outlined above, for certain examples of the invention along with comparative examples. The electrochemical window, viscosity and melting point data for these ionic liquids, is given in Table 1 below.

TABLE 1

| Example No. | Cation | Anion | EW in acetonitrile (V) | EW of neat IL (V) | Viscosity/cP at 25° C. | Melting point (° C.) |
|---|---|---|---|---|---|---|
| Comparative Example 1a | $C_4$mHMI | $Tf_2N$ | 6.5 | — | 236 | −80 |
| Comparative Example 1b | | TfO | † | † | † | 71 |
| Comparative Example 1c | | $CF_3CO_2$ | † | † | † | 78 |
| Example 1a | MeO($CH_2$)$_2$-mHMI | $Tf_2N$ | 5.5 | 5.75 | 134 | −75 |
| Example 1b | | TfO | 5.5 | — | 741 | −72 |
| Example 1c | | $CF_3CO_2$ | 5 | 5 | 434 | −72 |
| Example 2a | MeO($CH_2$)$_2$O($CH_2$)$_2$-mHMI | $Tf_2N$ | 6 | 6.25 | 38.2 | −82 |
| Example 2b | | TfO | 5.75 | — | 1074 | −68 |
| Example 2c | | $CF_3CO_2$ | 5.5 | 5.5 | 355 | −70 |
| Comparative Example 4 | $C_4$m3MP | $Tf_2N$ | 6.25 | — | 269 | −77 |
| Example 3 | MeO($CH_2$)$_2$O($CH_2$)$_2$-m3MP | $Tf_2N$ | 5.5 | 5.5 | 105 | −76 |
| Example 4 | MeO($CH_2$)$_2$-m3MP | $Tf_2N$ | 5.75 | 6 | 127 | −70 |

† Measurement of comparative data for the EW and viscosity of these ionic liquids was not possible owing to the fact that the compounds are solid at room temperature.

In the above table HMI=hexamethyleneimine, (also known as azepane); 3MP=3-methylpiperidine; m=methyl.

For example, MeO($CH_2$)$_2$O($CH_2$)$_2$-mHMI is 1-[2-(2-methoxyethoxy)ethyl]-1-methyl-azepanium, i.e., the cation shown below;

The invention claimed is:

1. An ionic liquid comprising a cation according to formula (I):

$$\begin{bmatrix} R^1 & R^2 \\ & N^+ \\ & \big)_n \\ R^3 & \end{bmatrix}$$
(I)

wherein:
n is 1 or 2;
$R^1$ is selected from H and ($C_1$-$C_6$)alkyl;
$R^2$ is selected from —($CH_2$)$_w$O[($CH_2$)$_x$O($CH_2$)$_y$]$_m$($CH_2$)$_2$$CH_3$ and —CH($CH_2$)$_w$O[($CH_2$)$_x$O($CH_2$)$_y$]$_m$$CH_2$, wherein w is 1 to 6, x is 1 to 6, y is 0 to 6, z is 0 to 6, m is 0 to 3 and
[w+m(x+y)+z] is less than or equal to 12; and
$R^3$ is selected from H and methyl, wherein
if n is 1 then $R^3$ is methyl, and
if n is 2 then $R^3$ is H.

2. The ionic liquid according to claim 1, wherein $R^2$ is —($CH_2$)$_w$O[($CH_2$)$_x$O($CH_2$)$_y$]$_m$($CH_2$)$_z$$CH_3$ and wherein w is 1 or 2, y is 0 to 2, z is 0 to 2 and m is 0 or 1.

3. The ionic liquid according to claim 2, wherein $R^2$ is selected from —($CH_2$)$_2$OMe or —($CH_2$)$_2$O($CH_2$)$_2$OMe.

4. The ionic liquid according to claim 1, wherein $R^1$ is methyl.

5. The ionic liquid according to claim 4, wherein n=2 and $R^3$ is H.

6. The ionic liquid according to claim 1, wherein the cation is selected from;
1-(2-methoxyethyl)-1-methylazepanium;
1-[2-(2-methoxyethoxy)ethyl]-1-methylazepanium;
1-(2-methoxyethyl)-1,3-dimethylpiperidinium; and
1-[2-(2-methoxyethoxy)ethyl]-1,3-dimethylpiperidinium.

7. The ionic liquid according to claim 6, wherein the viscosity of the liquid is less than 300 cP at 25° C.

8. The ionic liquid according to claim 7, wherein the viscosity of the liquid is less than 150 cP at 25° C.

9. The ionic liquid according to claim 8 further comprising an anion $X^-$, selected from:
bis(trifluoromethylsulphonyl)imide; dicyanamide; hexahalophosphates; tetrahaloborates; halides; nitrates; sulfates; phosphates; carbonates; sulfonates; carboxylates and silicates.

10. The ionic liquid according to claim 9, wherein $X^-$ is selected from bis(trifluoromethylsulphonyl)imide, dicyanamide, trifluoromethylsulphonate and trifluoroacetate.

11. The ionic liquid according to claim 10, wherein $X^-$ is bis(trifluoromethylsulphonyl)imide.

12. The ionic liquid according to claim 11 selected from 1-(2-methoxyethyl)-1-methyl-azepanium bis(trifluoromethylsulphonyl)imide; 1-[2-(2-methoxy-ethoxy)ethyl]-1-methyl-azepanium bis(trifluoromethylsulphonyl)imide; 1-(2-methoxyethyl)-1,3-dimethylpiperidinium bis(trifluoromethylsulphonyl)imide; and 1-[2-(2-methoxyethoxy)ethyl]-1,3-dimethylpiperidinium bis(trifluoro-methylsulphonyl)imide.

13. An electrochemical device comprising an ionic liquid according to claim 1.

14. The electrochemical device according to claim 13, wherein said device is an electrochemical double-layer capacitor (EDLC).

15. The electrochemical device according to claim 14, wherein said EDLC is an asymmetric electrochemical double-layer capacitor (AEDLC).

16. A hybrid electric vehicle (HEV) comprising the electrochemical device according to claim 15.

17. The use of an ionic liquid according to claim 1 as an electrolyte in an electrochemical device.

18. The use according to claim 17, wherein said device is an asymmetric electrochemical double-layer capacitor (AEDLC) in a hybrid electric vehicle (HEV).

19. A method for the preparation of an ionic liquid according to claim 1, said method comprising at least one N-substitution of the compound of formula (II):

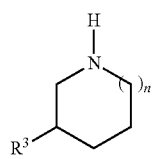

(II)

wherein;

n is 1 or 2, $R^3$ is selected from H and methyl, wherein;

if n is 1 then $R^3$ is methyl, and if n is 2 then $R^3$ is H.

20. The method according to claim 19, wherein the compound of formula (II) is a by-product of the manufacture of 1,6-hexanediamine.

21. The method according to claim 19, wherein the compound of formula (II) is a by-product of the manufacture of 2-methyl-1,5-pentanediamine.

* * * * *